United States Patent [19]

Larson et al.

[11] Patent Number: 5,378,531

[45] Date of Patent: Jan. 3, 1995

[54] GAMMA RADIATION TREATED SHEET MATERIAL FOR USE AS ORTHOPEDIC SPLINTS AND CASTS AND THE LIKE

[76] Inventors: Peter M. Larson, 2395 Charles St., Bexley, Ohio 43209; Lester M. Larson, 14110 White Rock Dr., Sun City West, Ariz. 85375

[21] Appl. No.: 89,729

[22] Filed: Jul. 9, 1993

[51] Int. Cl.⁶ .................... A61F 5/04; A61L 15/12; A61L 15/14; C08J 5/24
[52] U.S. Cl. ........................................ 428/255; 2/311; 12/146 D; 12/146 M; 12/142 N; 36/87; 36/154; 36/DIG. 2; 204/157.63; 381/187; 450/39; 450/57; 450/93; 528/359
[58] Field of Search ............... 602/7, 14; 528/359; 204/157.63; 2/311; 12/146 D, 146 M, 142 N; 36/87, 154, DIG. 2; 450/39, 57, 93; 428/542.8, 255

[56] References Cited

U.S. PATENT DOCUMENTS 4,240,415 12/1980 Wartman .
4,316,457 2/1982 Liegeois .

Primary Examiner—James C. Cannon
Attorney, Agent, or Firm—Connolly and Hutz

[57] ABSTRACT

Orthopedic splint materials made with thermoplastic polyester, particularly poly (epsilon-caprolactone) with a molecular weight of over 5,000 and melting between 50° C. and 100° C. have improved properties when subjected to gamma radiation in the range from 0.5 to 30 megarads.

12 Claims, 2 Drawing Sheets

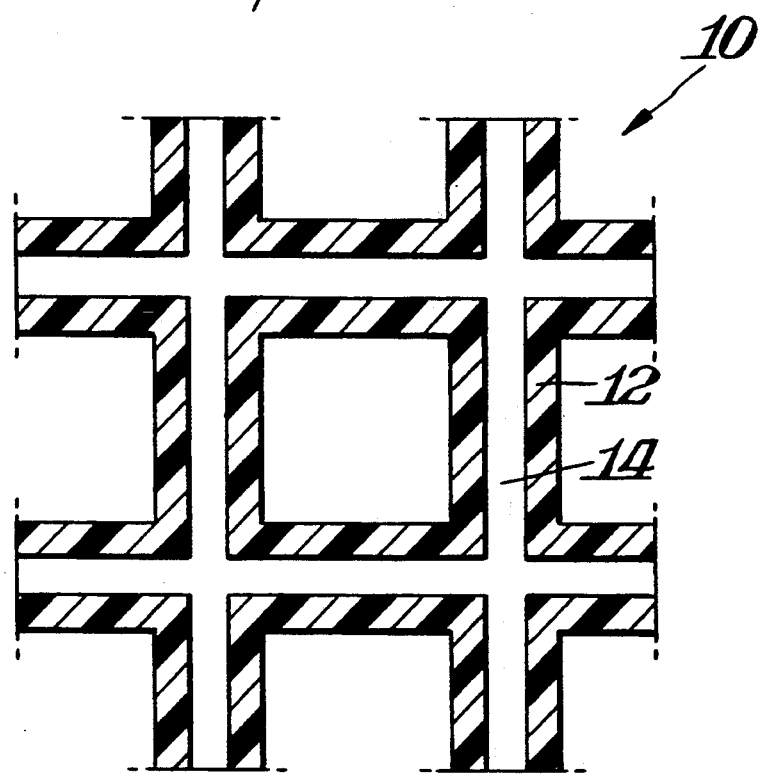

GAMMA RADIATION TREATED SHEET MATERIAL FOR USE AS ORTHOPEDIC SPLINTS AND CASTS AND THE LIKE

SUMMARY OF THE INVENTION

This invention relates to improved properties of materials for making body supporting splints, casts, or protective elements, such as shoes, brassieres, belts, athletic supporters, headphones, earphones, ear plugs, impression casting material for dentists, and the like, including moldable plastic storable in rolls, stacks or sheets or moldings from which individual moldable elements are readily separated and formed into shapes for such uses as listed.

Plastic materials have been successfully used in the past for making splints, casts and the like. U.S. Pat. No. 3,490,444 describes the use of thermoplastic polydienes like transpolyisoprene and transpolychloroprene which melt between 60° C. and 100° C. and harden by crystallization at about 40° C. whereby this can be formed for use as a body supporting member. An important feature of that invention is the incorporation of a filler (e.g. short lengths of fiber) such that the final product would be free of substantial creep or deformation under long periods of use below about 40° C. Other polymers melting between 50° C. and 110° C. and hardening by crystallization have also been recommended. U.S. Pat. No. 3,604,413 recommends copolymers of trioxane and several other polymers. Poly (epsilon-caprolactone) (PCL) has also been found to be an excellent splint or cast material (U.S. Pat. No. 4,144,223). Polyurethanes based on prepolymers of poly (epsilon-caprolactone) have also been used (U.S. Pat. No. 4,316,457).

As described in earlier patents, the polymers can be heated in hot water at a temperature usually exceeding 50° C. and up to about 100° C., whereby they become soft, self-adherent and pliable sufficient to be deformed and shaped as a cast or splint or protective device. When allowed to cool in air to about 40° C., the materials remain pliable, moldable and cohesive for a period of several minutes, exhibiting a hysteresis, as described in U.S. Pat. No. Re. 30,541. During this time the splint, east or device can be molded directly to the patient without discomfort, whereupon the so shaped plastic hard sets by crystallization to assume a rigid form as a useful body support member or protective device.

Poly (epsilon-caprolactone) is an excellent splint or cast material by itself and in blends with common, fine particle size fillers and pigments, such as silica, diatomaceous earth, clay, and titanium dioxide. The filler may be present in the blends at a concentration of from about 1 to about 30 parts by weight per 100 parts by weight of the poly (epsilon-caprolactone). Mixtures of the fillers may also be used, especially of silica and titanium dioxide, which impart a desirable white color to the compound.

Poly (epsilon-caprolactone) (PCL) makes an excellent cast or splint, in the hardened state. However, the heat-softened material is difficult to handle because it is fluid and sticky. This can be overcome by adding reinforcing fibers, cheesecloth (to support the plastic), or by blending PCL with a polymer like Transpolyisoprene (TPI), which is more elastic in the heat softened state.

Applicant Lester Larson has conducted laboratory investigations of the properties of PCL-TPI blends. The stickiness of heat-softened PCL disappears at around 50—50 mixtures, but other properties (e.g. tensile strength) are better when 25% or more of the blend is Transpolyisoprene. Pure PCL is good in respect to hardness, strength, hysteresis, and it has the advantage of being transparent in the heat-softened state. Fluidity and stickiness are its drawbacks. It has been found that this softened state fluidity is reduced by electron radiation of thin sheets of the polymer (U.S. Pat. No. 4,240,415).

SUMMARY OF THE INVENTION

An object of this invention is to provide techniques which improve upon those using electron radiation such as in U.S. Pat. No. 4,240,415.

A further object of this invention is to provide such techniques which could produce materials usable as support members such as orthopedic splints, casts, shoe inserts, arch supports and the like.

In accordance with this invention gamma radiation is used for treating the material. We have found that the heat softened properties of poly (epsilon-caprolactone) can be improved in a better way by irradiation with gamma rays.

Gamma radiation is different in kind from electron radiation. Beta rays (electron beams) interact with matter and transfer energy by collision. High speed electrons undergo relativistic effects and as they approach the speed of light, the electron mass approaches infinity. Gamma rays (x-rays) travel at the speed of light and interact with matter by resonance (they have O mass).

In this particular application the gamma radiation process has several advantages. Whereas electron beams penetrate matter only a few millimeters and can only be used on thin sheets openly exposed, gamma radiation is very penetrating. Much thicker mass can be treated. Stacks of PCL sheets 12 or more inches thick can be uniformly radiated by conventional means (e.g. using cobalt 60). Also, whereas electrons can only be used on open flat thin sheets, gamma radiation can be used on shaped objects, such as precut or preformed splints and customized supports like arch supports and show inserts.

Gamma radiation can also be applied to pre-boxed or pre-packaged materials. Having materials pre-packaged makes for easier handling and processing, and additionally, since gamma radiation in effect sterilizes these materials, the packaged sheets can remain essentially sterile until they are unwrapped by the end-user. This is especially useful in many critical care applications. The gamma radiation process is also less expensive than electron radiation. Commercial operations are well understood and are now being used (by us) for these purposes.

THE DRAWINGS

FIG. 3 is a cross-sectional view of a sheet formed in accordance with this invention.

DETAILED DESCRIPTION

The following examples illustrate the operation and practice of this invention:

EXAMPLE 1

Sheets of poly (epsilon-caprolactone) ⅛" thick were subjected to dosages of 0, 5, 10, 20, and 40 megarads of gamma radiation. The sheets were then cut into strips 6"×½×⅛". These strips were then dipped in hot water (at 160° F.) until they became fully softened and transparent (about 20 seconds), whereafter they were manipulated manually by pulling, stretching, bending, and forming into various shapes and allowed to cool and harden at room temperature.

Unradiated (0 megarads) PCL strips showed no resistance to pulling, when heated. Radiated strips developed a resistance to pulling, when heated. Radiated strips developed a resistance to pulling, directly in proportion to the amount of radiation dosages. This resistance is best described as an "elasticity", because the radiated strips tend to pull back to their original form when stretched.

Figure 1:
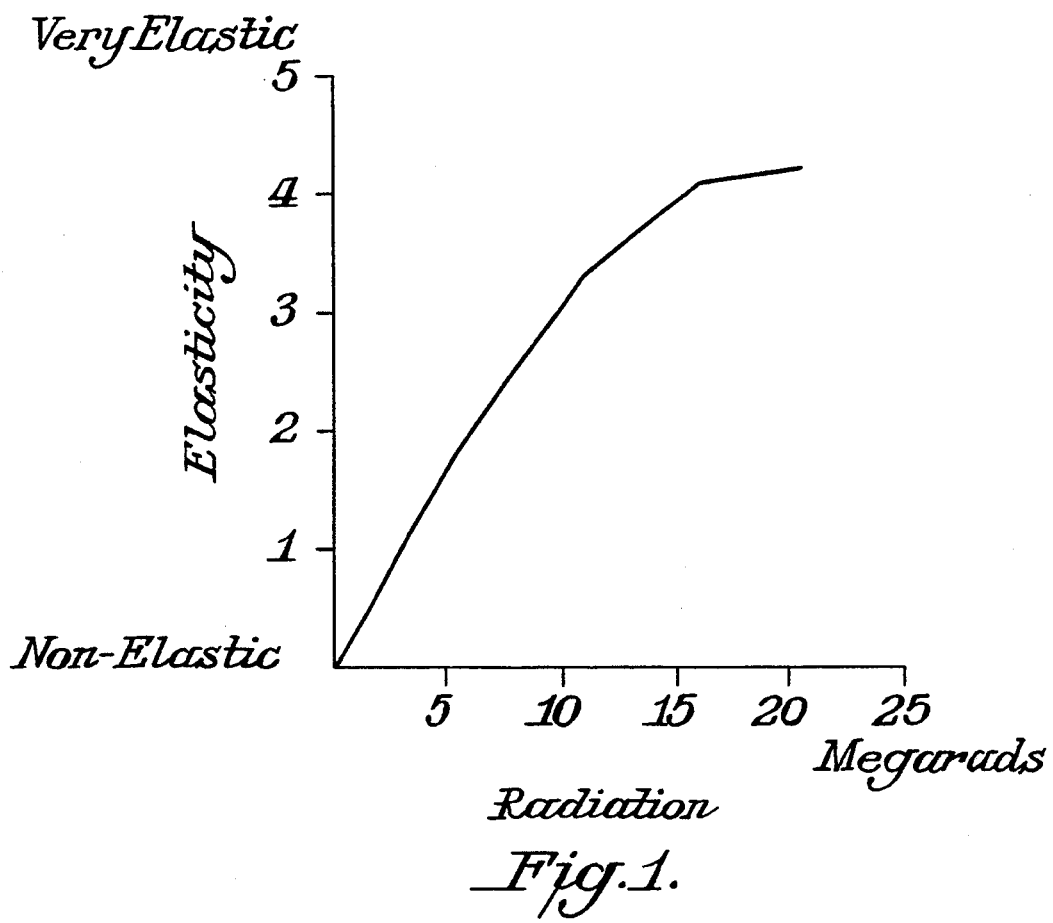
FIG. 1 is a graph showing elasticity properties with respect to gamma radiation.

FIG. 1 illustrates the observed elasticity.

Elasticity at level 0 means no observable elasticity when heated, as in unradiated samples. Unradiated strips can be stretched out with little to no resistance and have no tendency to pull back to their original shape. If stretched out, even slightly, they became almost liquid and would drip to the floor. Strips radiated at 5 megarads had a slight tendency to pull back to their original shape when stretched, and would not drip to the floor. 10 and 20 megarad strips became progressively more difficult to stretch out, but would not break off when stretched excessively, and if reshaped, would hold their reshaped configuration. Strips radiated at 40 megarads could not be lengthened. If pulled with an excess of at 25 pounds they would stretch less than 25% and break in two, with the ends snapping back to their original shape.

All samples showed no evidence of internal gassing as described from electron radiation in U.S. Pat. No. 4,240,415.

EXAMPLE 2

Sheets of polyurethanes based on prepolymers of poly (epsilon-caprolactone) are prepared as per U.S. Pat. No. 4,316,457 with a melting point of about 55° C. The material is extruded into sheets 24"×18"×⅛" which are subjected to dosages of 0, 5, 10, 20 and 40 megarads of gamma radiation. The sheets are then cut into strips 6"×½×⅛". These strips are then dipped in hot water (at 160° F.) until they become softened, whereafter they are manipulated manually by pulling, stretching, bending and forming into various shapes and allowed to cool and harden at room temperature.

Unradiated (0 megarads) strips show little to no resistance to pulling when heated and are too fluid to manipulate into shapes. Radiated strips develop a resistance to pulling, directly in proportion to the amount of radiation dosages. This resistance is best described as an "elasticity", because the radiated strips tend to pull back to their original form when stretched. The amount of elasticity induced by the radiation is measured to be similar to the elasticity induced in the strips of pure poly (epsilon-caprolactone) as in example 1.

EXAMPLE 3

Blends of poly (epsilon-caprolactone), silica and titanium dioxide were prepared in a mixture of 100 parts PCL to 20 parts silicon dioxide and 3 parts titanium dioxide. The mixture was extruded into sheets 24"×18"×⅛" which were subjected to dosages of 0, 5, 10, 20, and 40 megarads of gamma radiation. The sheets were then cut into strips 6"×½"×⅛". These strips were then dipped in hot water (at 160° F.) until they became fully softened (about 20 seconds) whereafter they were manipulated manually by pulling, stretching, bending, and forming into various shapes and allowed to cool and harden at room temperature.

Unradiated (0 megarads) strips showed no resistance to pulling, when heated. Radiated strips developed a resistance to pulling, directly in proportion to the amount of radiation dosages. This resistance is best described as an "elasticity", because the radiated strips tend to pull back to their original form when stretched. The amount of elasticity induced by the radiation was measured to be identical to the elasticity induced in the strips of pure poly (epsilon-caprolactone) as in example 1.

EXAMPLE 4

Poly (epsilon-caprolactone) is cut or formed to the shape of a shoe insert, arch support or insole, radiated with gamma radiation to a desired level of elasticity and then custom fitted by heat softening, allowing to cool, and molding directly to the contours of the wearer's

EXAMPLE 5

It is known that certain other polyesters can be cross-linked by ionizing radiation, particularly unsaturated polyesters in which the difunctional acid contains a double bond (e.g. derived from maleic, itaconic acid, etc.) In such materials, ionizing radiation initiates polymerization by forming free radicals which react with the double bonds in a way similar to the polymerization of a vinyl monomer.

The radiation dosage need to effect cross-linking can be reduced by incorporating certain additives into the poly (epsilon-caprolactone). The effective additives are chemicals containing two or more double bonds in each molecule.

The incorporation of 2-ethyl-2-(hydroxymethyl)-1-3-propanediol trimethacrylate at a level of 2% in poly (epsilon-caprolactone) reduces the dosage of gamma radiation required to cross-link the polymer by at least half. The incorporation of other polyunsaturated molecules, such as neoprene or butadiene rubbers also accelerate the cross-linking reaction.

EXAMPLE 6

Sheets of poly (epsilon-caprolactone) ⅛" thick were subjected to dosages of 0, 5, 10, 20, and 40 megarads of gamma radiation. The sheets were then cut into strips 6"×½"×⅛". These strips were then dipped in hot water (at 160° F.) until they became fully softened and transparent (about 20 seconds), whereafter they were manually stretched out to a length of 12 inches and allowed to cool and harden at room temperature, except for the 40 megarad strips which broke in two when stretched more than 25% of their length. The strips were then reheated in the hot water, whereupon the radiated strips tended to immediately shrink back to their original shapes, the amount of such tendency increasing directly proportional to the radiation levels of the strips.

Unradiated strips showed no such "melt-memory" tendency, and did not shrink back upon reheating. Strips at 5 megarads returned to a length of approximately 9 inches. Strips at 10 megarads returned to within an inch of their original length, and strips at 20 megarads returned almost 100% to their original length and width. In all radiated strips this "melt-memory" displayed itself immediately as the samples were dipped in the hot water.

Figure 2:
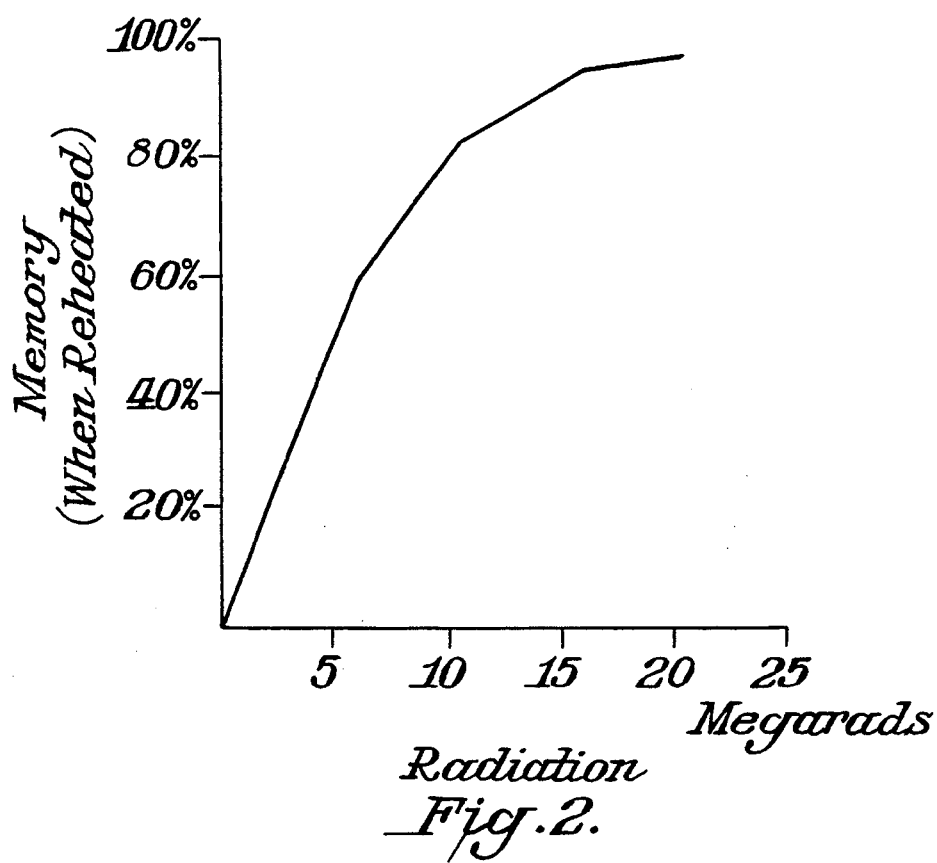
FIG. 2 is a graph showing memory properties with respect to gamma radiation.

FIG. 2 illustrates the melt memory for different levels of radiation.

EXAMPLE 7

Polymeric materials processing crystallinity, i.e. regions or regular structure in which the polymeric chains are closely packed, exhibit melting points. The enthalpy of melting or the heat required to convert the solid polymer to the liquid state is a direct measure of the crystallinity present. Further, when the liquid solidifies upon cooling, the heat of crystallinity is released by the polymer to its environment.

Any physical or chemical change to the polymer which inhibits crystallinity will lead to the decrease in the enthalpy of melting. For instance, polymer chains with side groups sticking out from the chain are likely to be less crystalline than linear chains materials. Alternatively, if the polymer chains of a crystalline polymer are tied together or cross-linked, then it may require more energy to cause disruption of the ordered polymer chains.

Differential scanning calorimetry (DSC) is an instrumental methodology which measures the enthalpies of melting and crystallization very accurately. Hence, it is a reasonable analytical tool to use when looking at the effect of radiation induced cross-linking upon crystalline polymers.

Samples of poly (epsilon-caprolactone) radiated at 0, 10 and 40 megarads or gamma radiation were analyzed with DSC to measure the initial heat of melting for the samples; with the following results:

| Sample | 1st Heat Enthalpy |
|---|---|
| 0 mrads | 77 J/g |
| 10 mrads | 80 J/g |
| 40 mrads | 84 J/g |

These first of enthalpies show a measurable but limited increase with increased radiation. This is consistent with increasing but limited polymer cross-linking with increased dosage of gamma radiation.

EXAMPLE 8

100 PCL sheets 18"×24"×⅛" were packaged in boxes (4 sheets per box); those boxes placed together in a mechanical carrier and conveyed around a cobalt-60 source until a uniform dosage of 10 megarads of gamma radiation was achieved, as measured by dosimeters strategically placed on the packages. Sheets were then removed, heat softened, cut to shape and formed into a variety of orthotic splints, and applied to patients by professional medical therapists.

EXAMPLE 9

Three preformed "cock-up" wrist splints made from ordinary PCL ⅛" thick sheets which had not been irradiated were placed in a cardboard box and subjected to cobalt 60 gamma rays until strategically placed dosimeters indicated a uniform dosage of 10 megarads. These irradiated "preforms" were then heat softened and fitted closely to a patient's wrist by conventional heat softening, fitting and cooling to hardness. This procedure enabled the therapist to form and customize the splint quickly and easily by reshaping the "preform" instead of having to start from a plain sheet, cutting and shaping it. Subtle adjustments to customize the fit of the "preform" are made without the material becoming liquid or losing it's basic shape. It is economical in that there is little or no waste or material. The preform needs little or no trimming.

EXAMPLE 10

This example had as its object to determine the effect of gamma radiation on medical splinting sheets made of poly (epsilon-caprolactone), a thermoplastic polyester having a melting point between 50° C. and 90° C.

METHOD

Four sheets, 12"×12"×⅛", of poly(epsilon-caprolactone were repeatedly passed by a cobalt 60 source, until the following dosages were reached for each of the four sheets:

Sheet #1 - 6.28 megarads
Sheet #2 - 11.50 megarads
Sheet #3 - 16.35 megarads
Sheet #4 - 20.15 megarads The sheets were then cut into one-inch strips and melted one at a time in a hot water bath at 70° C. Strips were then manipulated, manually distorted into various shapes, and cooled to room temperature. Then they were reheated and manipulated again. Throughout this process, observations were made as to the tensile strength, stiffness, elasticity, moldability, and "memory" (i.e. the tendency to return to its original shape when reheated), for strips from each of the different sheets. Differences in the performance of the samples are then attributed to the effect of gamma radiation at the different levels. A control sample, which was given no radiation, was also used.

OBSERVATIONS

The two most dramatic changes caused by gamma radiation appear to be increased elasticity in the materials molten state, and "memory" when sample are reheated.

First, elasticity:
When non-radiated strips are heated they become almost liquid. They can be stretched easily. They lose their shape immediately, and if a strip is held firmly at one end, the other end will drip all the way to the floor.

Strips from sheet #1 however did not drip, could be stretched fairly easily, but had an elastic tendency to resist stretching to some degree. When heated, strips from sheet #2 had a markedly stronger elasticity. They could be stretched, but only by pulling with some strength, and they had a tendency to return to their original shape unless held in the new position until the samples cooled and hardened.

When heated, strips from sheets #3 and #4 behaved almost identically. They displayed a little more elasticity the #2 strips, and were a little tougher to stretch. However, the increased elasticity of #3 and #4 was slight, compared to the difference between #1 and #2,

"MEMORY"

When non-radiated sheets were heated, stretched and cooled, and then re-heated, they exhibited no tendency to return to their original shape, i.e. no memory.

When #1 strips were similarly treated, they quickly shrank back to their original shapes.

The same was true for #2, #3, and #4 strips. They did seem to shrink back more quickly than the #1 strips, but even the #1 strips returned quickly to their original shape.

TENSILE STRENGTH

When heated, non-radiated strips became almost liquid, with no tensile strength. #1 strips required a little pull to stretch them out when heated . . . #2 strips much more pull . . . and #3 and #4 strips were a little tougher yet, requiring some real strength to stretch them out. #3 and #4 were roughly identical in this area.

In their cooled, hardened states, all samples, including the non-radiated samples seemed to have hardness, stiffness, and tensile strength, i.e. they could not be stretched by hand.

MOLDABILITY

Non-radiated pieces were very moldable when heated. However, their tendency to run and drip makes them less than desirable for making splints. The runniness creates a "pizza dough" effect leaving thin spots, and weak spots in molded pieces, unless the person doing the molding is very skilled and very careful. This "pizza dough" effect disappeared in all the radiated samples. #1 strips were easy to mold into any shape when heated, but had a "flimsy" feel to them until they cooled and hardened. #2 strips had more tendency to spring-back, and resisted molding a bit, but they hold their thickness more uniformly and had a good substantial feel, when pushed into a new shape. #3 and #4 strips were difficult to mold when heated. Their tendency to spring back made it almost impossible to give them a new shape, without having to grip them tightly all through the cooling process, till they hardened.

CONCLUSIONS

The changes induced by gamma radiation are consistent with a conclusion that cross-linking has occurred in the poly (epsilon-caprolactone). It appears this cross-linking starts at a dosage less than 6 megarads, and reaches a saturation point somewhat around 15 megarads. This is obviously a rough estimate, based on the above subjective observations. This cross-linking is a substantial improvement in this material, for the purpose of making medical splints and casts. By controlling the amount of gamma radiation, it will be possible to market a product (or products) with a desired amount of moldability and memory.

Because of the penetrating nature of gamma radiation, it should be possible to radiate sheets in bulk. This would be an economically advantageous process. An additional advantage is that gamma radiation would also render the sheets sterile, an obvious benefit their intended medical use..

FIG. 3 illustrates a sheet 10 in accordance with this invention. As shown therein the poly (epsilon-caprolactone) material 12 is coated on a substrate 14. Where the sheet 10 is used as an orthopedic cast, the substrate 14 may be a netting and the polyester 12 would be coated around each strand to form a foraminous sheet 10.

The invention may also be broadly practiced using the techniques described in U.S. Pat. No. 4,240,415 (the details of which are incorporated herein by reference thereto) except that gamma radiation would be used instead of electron radiation.

The advantageous properties of sheets produced by the invention may be used in a wide variety of products of otherwise conventional construction particularly for support purposes. Such products include orthopedic splints, casts, shoe inserts and arch supports. Other protective elements which make use of the invention include shoes, brassieres, belts, athletic supporters, headphones, earphones, ear plugs, and dental impression casting materials. The sheets of the invention may be moldable plastic storable in rolls, stacks or sheets or moldings from which individual moldable elements may be readily separated and formed into shapes.

What is claimed is:

1. A method of radiating sheets or numbers of preformed items of poly (epsilon-caprolactone) with gamma radiation, by packaging the sheets or numbers of preformed items in bulk to form packages, and subjecting the packages to gamma radiation until the radiation dosage reaches a range of from about 0.5 to about 20 megarads as measured by strategically placed dosimeters.

2. A method as recited in claim 1, wherein the support sheet is selected from the group consisting of orthopedic splints, casts, shoe inserts, arch supports, shoes, brassieres, belts, athletic supporters, headphones, ear plugs and dental casting materials.

3. A method as recited in claim 1, wherein the sheets are comprised of a blend of poly (epsilon-caprolactone), containing up to about 30 parts of fine particle size fillers and/or pigments, per 100 parts of poly (epsilon-caprolactone).

4. A method as recited in claim 3, wherein the support sheet is selected from the group consisting of orthopedic splints, casts, shoe inserts, arch supports, shoes, brassieres, belts, athletic supporters, headphones, ear plugs and dental casting materials.

5. A method as recited in claim 1, wherein the sheets are a polyurethane based on prepolymers of poly (epsilon-caprolactone).

6. A method as recited in claim 5, wherein the support sheet is selected from the group consisting of orthopedic splints, casts, shoe inserts, arch supports, shoes, brassieres, belts, athletic supporters, headphones, ear plugs and dental casting materials.

7. A method as recited in claim 1, wherein the sheets contain a mixture of at least about 95%, poly (epsilon-caprolactone), and an effective amount up to about 5% 2-ethyl-2-(hydroxymethyl)-1-3-propanediol trimethacrylate.

8. A method as recited in claim 7, wherein the support sheet is selected from the group consisting of orthopedic splints, casts, shoe inserts, arch supports, shoes, brassieres, belts, athletic supporters, headphones, ear plugs and dental casting materials.

9. A method as recited in claim 1, wherein the sheets contain a mixture of at least about 90% poly(epsilon-caprolactone), blended with an effective amount up to about 10% of a cross-linking agent.

10. A method as recited in claim 9, wherein the support sheet is selected from the group consisting of orthopedic splints, casts, shoe inserts, arch supports, shoes, brassieres, belts, athletic supporters, headphones, ear plugs and dental casting materials.

11. The method as claimed in claim 9, wherein said cross-linking agent is neoprene.

12. A sheet of material provided by the process of claim 1.

* * * * *